United States Patent
Lin et al.

[19]

[11] Patent Number: 6,137,708
[45] Date of Patent: Oct. 24, 2000

[54] METHOD FOR FORMING MULTI-CHIP SENSING DEVICE AND DEVICE FORMED

[75] Inventors: Yuh-Jiuan Lin; Ming-Chang Shih, both of Taipei; Kuo-Chuan Chen, Hsin chu; Tzong-Zeng Wuh, Taipei, all of Taiwan

[73] Assignee: Industrial Technology Research Institute, Hsin Chu, Taiwan

[21] Appl. No.: 09/141,204

[22] Filed: Aug. 27, 1998

[51] Int. Cl.$^7$ .................................................. G11C 7/00
[52] U.S. Cl. ................................ 365/51; 365/52; 257/700
[58] Field of Search ................................ 365/51, 52, 63; 257/700

[56] References Cited

U.S. PATENT DOCUMENTS 6,023,097   2/2000   Chiang et al. ............................. 365/51

*Primary Examiner*—Terrell W. Fears
*Attorney, Agent, or Firm*—Tung & Associates

[57] ABSTRACT

A multi-chip sensing device package and a method for forming such package are disclosed. The multi-chip sensing device package is built on an electrically insulative substrate such as a ceramic material, by using a thick film printing technique to print a multiplicity of bonding pads including interconnection pads and output pads on the surface of the rigid, insulated substrate. After a plurality of sensing elements are bonded by solder to the plurality of bonding pads, the sensing device may be connected to either lead fingers of a lead frame, or to J-leads formed integral with the device for providing electrical communication with an external circuit. The device may further be packaged in a plastic housing with a top surface of the device exposing to the environment for performing its detection function.

19 Claims, 3 Drawing Sheets

METHOD FOR FORMING MULTI-CHIP SENSING DEVICE AND DEVICE FORMED

FIELD OF THE INVENTION

The present invention generally relates to a method for packaging multi-chip sensing device and device formed and more particularly, relates to a method for forming multi-chip sensing device on an insulating substrate and providing external communication with the device through lead fingers or J-leads connected to output pads on the device and device formed by such method.

BACKGROUND OF THE INVENTION

In recent years, advancement made in biotechnologies has developed various new methods for detecting breath metabolites that are related to diseases. These new developments in technologies have made possible direct and fast responding techniques for detection. For instance, in a co-pending application assigned to the common assignee of the present application, Attorney Docket No. 64,600-024 which incorporated hereby in its entirety by reference, a system and method for modeling peptides to cover an artificial nose have been proposed. The artificial nose equipped with sensing films can be used to detect various forms of human diseases by detecting specific chemical species of exhaled gases that are associated with such diseases. In most circumstances, in order to detect a certain physical condition or a disease, a number of chemical species must be detected. Since the peptides developed to cover an artificial nose can be used to identify only one type of gas molecules associated with a certain smell, a number of artificial nose that are packaged in separate sensing elements must be used to accommodate the different peptides required for sensing the various types of gas molecules. In order to put the artificial nose to practical use, the various sensing films containing peptides as a cover for an artificial nose must be packaged together in a single unit so that it can be used to monitor and detect the various gases simultaneously. When the use of such a detection unit is mobile, the unit should be designed in a compact size so that it can be moved and carried easily. The packaging of a multiple number of sensing elements in a small and compact unit is therefore an important aspect of the technology that must be developed before it can be put to practical use.

In packaging a number of sensing elements, or chips, into a small and compact unit, conventional technology used for packaging microelectronic IC chips into a so-called multi-chip module is first considered. However, the multi-chip modules developed in the semiconductor industry requires the multiple number of IC chips be encapsulated completely and therefore sealed in an insulative material. This makes it impossible for the detection of gas molecules by the sensing elements since the elements would be encapsulated in a solid insulative material such as a polymer. The conventional multi-chip module used in the semiconductor industry therefore does not provide a package that leaves an access to the sensing elements. Furthermore, since the detection of specific gas molecules associated with a biological condition requires extremely high sensitivity in order to detect a minute amount of the gas, the effect of any noise signals produced by a poorly designed package is detrimental to the proper functioning of the sensing elements. The conventional multi-chip modules are not designed for minimizing noise signals, specifically at its output terminals. A new method for packaging which minimizes noise signals produced either inside the package or at the output terminals must be provided before the package can be reliably used in biomedical type of detections.

It is therefore an object of the present invention to provide a method for forming a multi-chip sensing device that does not have the drawbacks or shortcomings of the conventional methods.

It is another object of the present invention to provide a method for forming a multi-chip sensing device that is equipped with an open front such that the sensing elements may detect gas molecules that the devices are exposed to.

It is a further object of the present invention to provide a multi-chip sensing device wherein noise signals generated at the output terminals of the device is minimized.

It is another further object of the present invention to provide a method for forming a multi-chip sensing device that is capable of accommodating a multiple number of sensing elements in a compact package.

It is still another object of the present invention to provide a multi-chip sensing device by mounting a multiple number of sensing elements to an electrically insulative substrate.

It is yet another object of the present invention to provide a multi-chip sensing device by providing a plurality of bonding sites on a ceramic substrate wherein each site includes at least two interconnection pads and two signal output pads formed of an electrically conductive metal.

It is still another further object of the present invention to provide a method for fabricating a multi-chip sensing device by forming interconnection pads and signal output pads on a ceramic substrate by a thick film printing technique.

It is yet another further object of the present invention to provide a method for fabricating a multi-chip sensing device by bonding a multiple number of sensing elements to a multiple number of bonding sites built on a ceramic substrate by a solder containing Sn and Pb.

SUMMARY OF THE INVENTION

In accordance with the present invention, a method for forming a multi-chip sensing device for packaging a multiple number of sensing elements and devices formed by such method are disclosed.

In a preferred embodiment, a multi-chip sensing device is provided which includes an electrically insulative substrate, a plurality of bonding sites situated on the substrate, each of the bonding sites includes at least two interconnection pads adapted for providing electrical communication with a sensing element and at least two signal output pads adapted for outputting signals from the sensing device, the pads are made of a metal that has high electrical conductivity, and a plurality of sensing elements bonded to the plurality of bonding sites.

The multi-chip sensing device may further include a multiplicity of lead fingers emanating from a lead frame that are bonded to the at least two signal output pads for providing external communication to the multi-chip sensing device. The electrically insulative substrate may be formed of a ceramic material, or may be formed of aluminum oxide. The interconnection pads and the signal output pads may be formed of a silver alloy, including silver/palladium alloy. The plurality of sensing elements are adapted for sensing gas or liquid.

The multi-chip sensing device may also include a plurality of sensing elements that are selected from the group consisting of a piezoelectric quartz crystal sensor, a MOS IC sensor and a surface acoustic wave (SAW) sensor. The plurality of sensing elements are bonded to the plurality of bonding sites by a solder containing Sn and Pb. The multi-chip sensing device may further include a multiplicity of J-leads bonded to the at least two signal output pads for providing external communication to the multi-chip sensing device. The multi-chip sensing device may further include a housing member of insulative material encasing the device with top surfaces of the plurality of sensing elements exposed.

In another preferred embodiment, a multi-chip sensing device package is provided which includes a ceramic substrate that is non-electrical-conductive, a plurality of bonding sites on the substrate each adapted for receiving a sensing element thereon, at least two interconnection pads adapted for electrical communication with the sensing element situated on each of the bonding sites, at least two signal output pads adapted for outputting signals from the sensing element situated on each of the bonding sites, a plurality of sensing elements bonded to the plurality of bonding sites, and an insulative housing encasing the multi-chip sensing device while exposing active elements in the plurality of sensing elements.

The multi-chip sensing device package may have a ceramic substrate that is formed of $Al_2O_3$. The at least two interconnection pads and the at least two signal output pads may be formed of Ag/pd. The plurality of sensing elements may be adapted for sensing a gas or a liquid. The plurality of sensing elements may be selected from the group consisting of a piezoelectric quartz crystal sensor, a MOS IC sensor and a surface acoustic wave sensor. The plurality of sensing elements are bonded to the plurality of bonding sites by a solder containing Sn and Pb.

The multi-chip sensing device package may further include a multiplicity of lead fingers emanating from a lead frame bonded to the at least two signal output pads for providing electrical communication with the multi-chip sensing device package. The multi-chip sensing device package may further include a multiplicity of J-leads bonded to the at least two signal output pads for providing electrical communication with the multi-chip sensing device package.

The present invention is further directed to a method for forming a multi-chip sensing device that can be carried out by the operating steps of first providing a non-electrical-conductive substrate, then forming a plurality of bonding sites on the substrate by the steps of, for each bonding site, depositing at least two interconnection pads of a high conductivity metal, depositing at least two signal output pads of a high conductivity metal, then connecting electrically at least one sensing element to the at least two interconnection pads, and connecting electrically at least two connection means to the at least two signal output pads.

The method for forming a multi-chip sensing device may further include the step of providing an $Al_2O_3$ substrate. The at least two connection means in the method may be a multiplicity of lead fingers emanating from a lead frame for providing external communication to the multi-chip sensing device. The at least two connection means may further be a multiplicity of J-leads for providing external communication to the multi-chip sensing device.

The method for forming a multi-chip sensing device may further include the step of forming the at least two interconnection pads with Ag/pd. The method may further include the step of depositing the at least two signal output pads with Ag/pd paste by a thick film printing technique. The method may further include the step of selecting the at least one sensing element from the group consisting of a piezoelectric quartz crystal sensor, a MOS IC sensor and a surface acoustic wave sensor. The method may further include the step of connecting electrically the at least one sensing element to the at least two interconnection pads by a solder containing Sn and Pb. The method may further include the step of connecting electrically at least two lead fingers emanating from a lead frame to the at least two signal output pads by a solder containing Sn and Pb.

BRIEF DESCRIPTION OF THE DRAWINGS

These and other objects, features and advantages of the present invention will become apparent from the following detailed description and the appended drawings in which.

DETAILED DESCRIPTION OF THE PREFERRED AND ALTERNATE EMBODIMENTS

Figure 1:
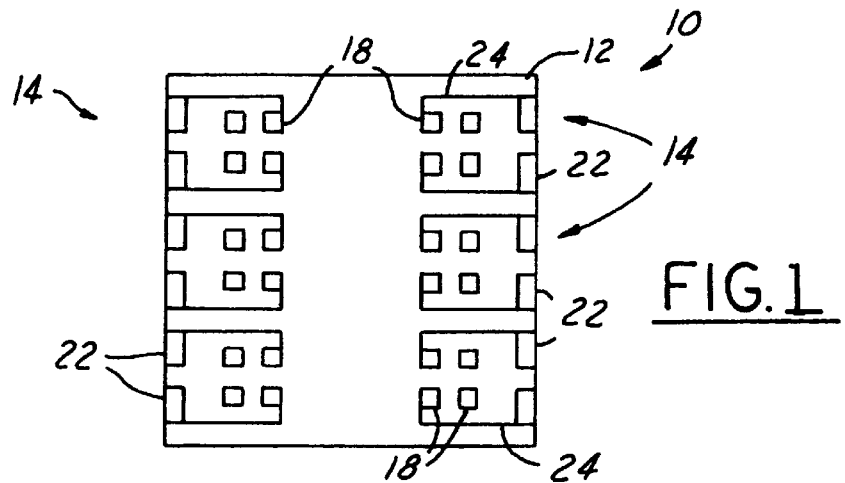
FIG. 1 is an enlarged, plane view of a substrate formed with interconnection pads and signal output pads for the present invention multi-chip sensing device.

The present invention discloses a multi-chip sensing device package, and a method for fabricating such package. The package is built on an electrically insulative substrate such as a ceramic substrate of $Al_2O_3$. A multiple number of bonding sites are provided on the ceramic substrate such that each of the sites being equipped with at least two interconnection pads and at least two signal output pads that are formed of a high electrical conductivity metal. The at least two interconnection pads may be suitably four interconnection pads that are adapted for providing electrical communication with a sensing element to be mounted on top of the site. The at least two signal output pads are adapted for outputting signals from the sensing device through the interconnection pads and a connecting circuit. The multi-chip sensing device further includes a multiple number of sensing elements each capable of sensing molecules of a specific gas by a film mounted on an artificial nose, or a sensing element. Each of the sensing elements is then bonded to one of the bonding sites by a solder containing Sn and Pb.

The communication with an external circuit for the multi-chip sensing device may be provided in one of several ways. For instance, a multiplicity of lead fingers may be bonded to the signal output pads on the multi-chip sensing device for providing external communication to the device. In another method, a multiplicity of J-leads may be formed and connected to the signal output pads for making external connections. In still another method, the finger leads may be formed in straight legs for connecting to plated through-holes in a printed circuit board.

The present invention multi-chip sensing device provides a suitable package for housing a multiple number of sensing elements which are normally required in utilizing microelectronics in biomedical applications. For instance, to detect a specific physical condition of a patient, a number of gas molecules need be monitored and detected from a patient's breath. The molecules may be detected by a number of sensing elements since each element only detects a single species of gas. This is because that each sensing element, or each artificial nose, is coated with a specific film containing peptide which can be used to absorb only one type of gas molecules. For certain biomedical applications, as many as 8, 16 or 32 different species of molecules must be detected. The present invention multi-chip sensing device package therefore provides a suitable platform for such applications even when as many as 32 sensing elements must be accommodated in a single sensing device.

In addition to the artificial nose utilized, any other forms of sensing elements may be suitably utilized in the present invention multi-chip sensing device package. For instance, a most likely used sensing element is a piezoelectric quartz crystal sensor that is effective in detecting absorption of molecules in a surface layer and detecting the change in its mass. The change in the mass of the surface of piezoelectric quartz crystal is then converted to a change in its oscillation frequency and correspondingly, a change in its electrical characteristics. For instance, an increase in the mass of the surface layer would result in a decrease in the oscillation frequency of the piezoelectric quartz crystal. The magnitude of the frequency drop can then be used to calculate the amount of absorption in the surface layer of the piezoelectric quartz crystal which is then used to calculate the concentration of the gas molecules that it detects.

The present invention multi-chip sensing device therefore utilizes an insulative substrate as a support, a base or a carrier for sensing elements of various types. The substrate is provided by a thick film printing technique with electrodes on its top surface as interconnection pads and signal output pads. The interconnection pads may be suitably formed of a high electrical conductivity metal such as silver or a silver alloy containing pallidum. The interconnection pads are connected to the sensing element such that the results of detection by the sensing element may be outputted through the signal output pads. The formation of the interconnection pads or the signal output pads may also be accomplished by techniques other than the thick film printing method, for instance, by sputtering through a mask.

Other sensing elements which are not piezoelectric quartz crystal sensors may also be utilized. One of such sensors is a MOS integrated circuit chip which can be used to measure a change in the electrical current instead of a change in frequency such as that performed by the piezoelectric sensors. Another sensing element of a surface acoustic wave (SAW) sensor may also be used in the present invention multi-chip sensing device package.

The advantages made possible by the present invention multi-chip sensing device package are numerous. First, the package produces a lower noise signal and thus higher detection efficiency, making it capable of detecting a minuet amount of molecules from the gas or liquid. The low noise generation is attributed by the use of novel connection methods for the multi-chip sensing device such as by lead fingers or by J-leads. Secondly, the present invention multi-chip sensing device package may be provided in an extremely small and thin package such that it can be easily used in the field as a portable unit. Thirdly, the present invention multi-chip sensing device package allows a large number of, for instance, as many as 32, sensing elements to be bonded thereto and thus performing multiple functions in detecting a variety of molecules in either a gas or a liquid. Furthermore, the present invention device package has great flexibility when connected to an external circuit. For instance, it may be connected by the use of lead fingers, by the use of J-leads, or by the use of straight pins and plated through-holes. The device package may further be connected as a surface mount device (SMD) by J-leads or connected in a flexible circuit (i.e., in a flexible circuit board) for use in palm-sized electronic devices.

Referring initially to FIG. 1, wherein an enlarged, plane view of a present invention multi-chip sensing device 10 is shown. The multi-chip sensing device 10 is constructed by a substrate 12 which is made of an electrically insulative material. A suitable electrically insulative material may be a ceramic such as aluminum oxide. The material should have sufficient rigidity to provide stability to the plurality of bonding sites 14 on the substrate 12. As shown in FIG. 1, each of the bonding sites 14 may be formed by a thick film printing technique with a multiplicity of bonding pads on the surface of the substrate 12. For instance, a multiplicity of interconnection pads 18 may be first formed for providing electrical communication with a subsequently bonded element (not shown). The thick film printing method is further used to provide signal output pads 22 for each of the bonding sites 14. The signal output pad 22 may be connected to the interconnection pad 18 by a circuit connection 24. The bonding pads 18 and 22 can be suitable formed of silver, or a silver alloy. For instance, a silver alloy that contains palladium. It should be noted that the term bonding pads is used to include both the interconnection pads 18 and the signal output pads 22. After the bonding pads 18, 22 are formed on the surface of the ceramic substrate 12, an electrically insulating material layer such as a polymer layer may be deposited in selected areas on the surface of the substrate 12 to either protect the pads or to provide a suitable mounting site for the sensing elements. The use of the ceramic substrate, such as an oxide material of $Al_2O_3$, significantly reduces any noise signal generation from the multi-chip sensing device package. The bonding pads may also be formed of a copper material or of copper alloys, even though the processing steps may be more complicated to carry out.

Figure 2:
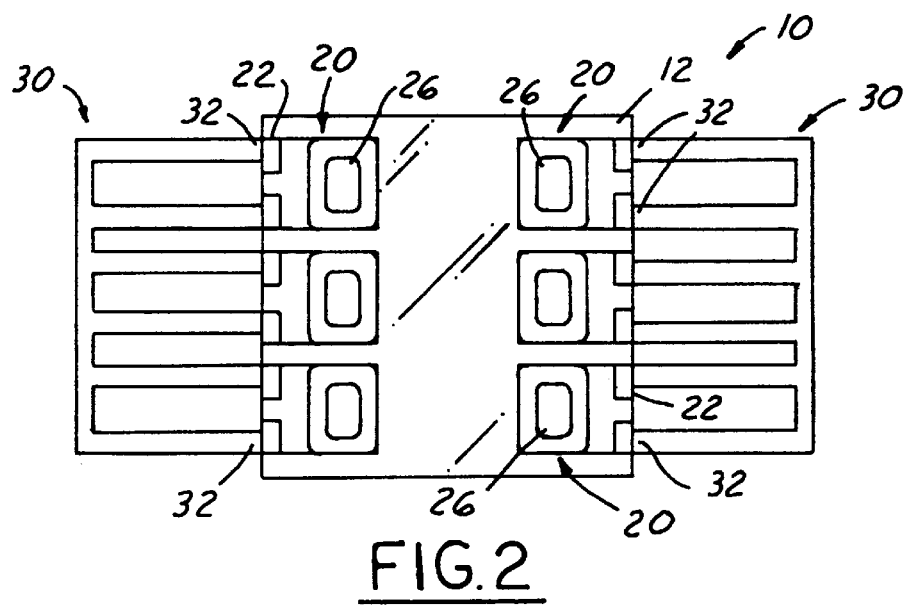
FIG. 2 is an enlarged, plane view of the substrate of FIG. 1 with a plurality of sensing elements and lead fingers bonded thereto.

In the next step of the process, as shown in FIG. 2, a plurality of sensing elements 20 are mounted on each of the bonding sites 14 by bonding to the interconnection pads 18. The bonding can be accomplished by using a solder material containing Sn and Pb. As shown in FIG. 2 in a plane view, the sensing elements 20 are piezoelectric quartz crystal sensors equipped with an open window portion 26 on a top surface of the element 20. The window 26 provides access of the sensing element to the external environment such that molecules of gas or liquid may be detected. The window portion 26 can further be protected by a protective film such that the sensing element is not damaged by dust, abrasion or other external elements.

As shown in FIG. 2, a lead frame 30 is further provided which is equipped with a multiplicity of lead fingers 32 each connected to an output pad 22 for providing external communication with a multi-chip sensing device 10. The lead frame 30 and the lead fingers 32 may be suitably formed of a metal foil that has high electrical conductivity. A suitable material for forming such foil is copper or copper alloys. The lead fingers 32 may be suitably connected to the signal output pads 22 by a conventional solder material containing Sn and Pb. A lead-free type solder may also be utilized for such bonding purpose. It should be noted that the lead frame or lead finger bonding method is merely one possible method for providing external communication with the present invention device 10. After the lead fingers 32 are bonded to the signal output pads 22, the device 10, together with the lead frame 30 may be annealed in an anneal oven at a suitable temperature to reduce the bonding stress and to improve the bond strength.

Figure 2A:
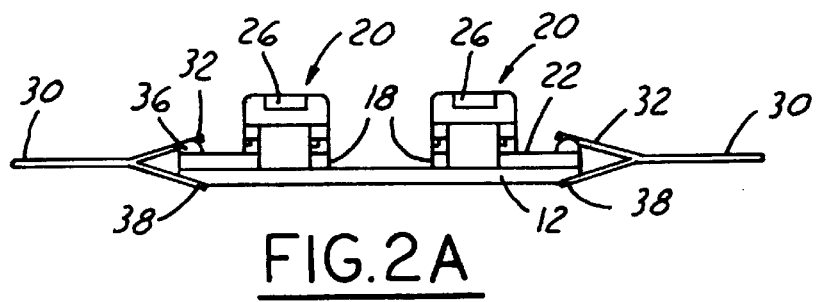
FIG. 2A is an enlarged, cross-sectional view of the structure of FIG. 2 with the output pads bonded to the lead frame.

An enlarged, cross-sectional view of the bonded structure 10 of FIG. 2 is shown in FIG. 2A. It is noted that the lead frame 30 is bonded, through lead fingers 32 to the signal output pad 22 by a solder ball 36. An opposite lead finger 38 which is electrically non-active is used as a mechanical clamping device to further stabilize the bonding formed between the lead finger 32 and the output pad 22 by clamping onto the rigid ceramic substrate 12.

Figure 2B:
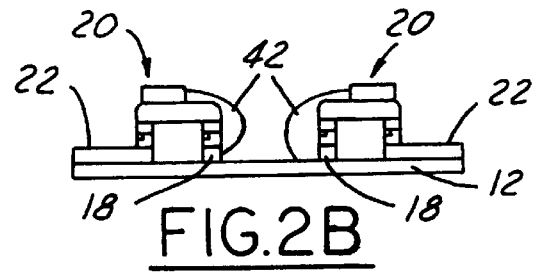
FIG. 2B is an enlarged, cross-sectional view of an alternate embodiment of the present invention device without using lead frame.

In an alternate embodiment, as shown in FIG. 2B, an enlarged, cross-sectional view is shown in which a solder material 42 is utilized for providing electrical communication between the sensing element 20 and the interconnection pads 18. The use of lead fingers and lead frame is therefore not necessary in this alternate embodiment. The signal output pads 22 may be bonded to an external circuit by various means.

Figure 3:
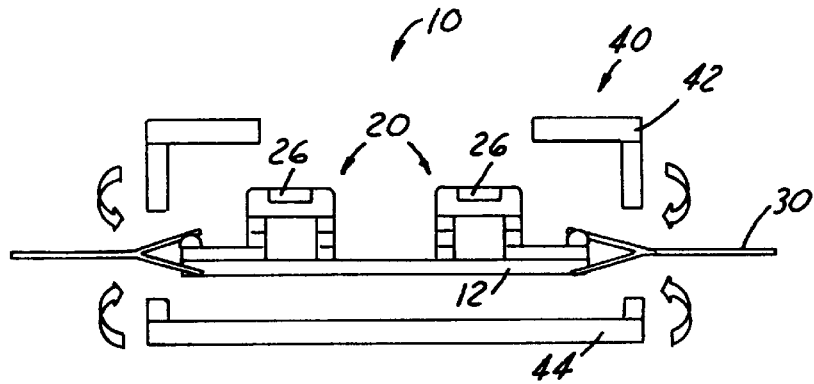
FIG. 3 is an enlarged, cross-sectional view of the present invention multi-chip sensing device bonded to lead fingers and positioned in a plastic housing.

To ensure a reliable service life of the present invention multi-chip sensing device 10, the device can be suitably bonded in a plastic housing 40 as shown in FIG. 3. The plastic housing 40 consists of an upper housing 42 and a lower housing 44. It is similar to a quad-flat-pack utilized in the semiconductor industry, except that the top of the upper housing 42 is open such that the top surfaces of the sensing elements 20 may be exposed to the environment. This makes it possible for the sensing elements to detect molecules and thus performing its sensing function. As seen in FIG. 3, the lead frame 30 protrudes outside the housing 40 such that, after the upper housing 42 and the lower housing 44 are bonded together, electrical communication with the external circuit can be made by the lead frame 30.

Figure 3A:
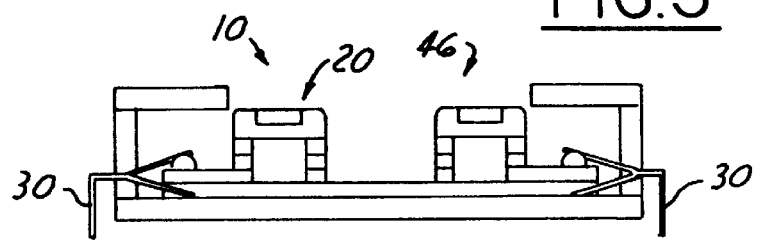
FIG. 3A is an enlarged, cross-sectional view of the structure of FIG. 3 after the plastic housing is bonded together and the lead fingers are shaped for connecting to plated through-holes.
Figure 3B:
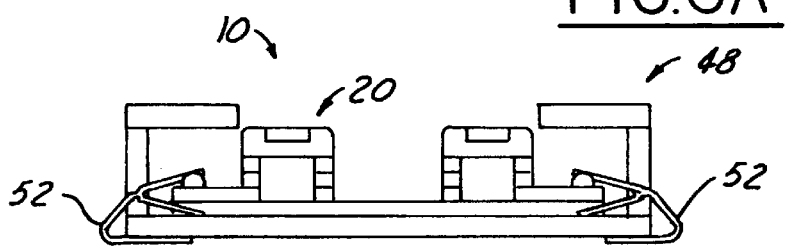
FIG. 3B is an enlarged, cross-sectional view of the structure of FIG. 3 after the plastic housing is bonded together and the lead frame are formed in J-leads.

Plastic housing protected packages 46 and 48 are shown in FIGS. 3A and 3B respectively. In the configuration 46 shown in FIG. 3A, the lead frame 30 is bent downwardly to provide a straight leg for connecting to a plated through-hole (PTH) on a printed circuit board. This is a connection method that can be easily performed. In the configuration shown in FIG. 3B, the plastic protected package 48 is provided with J-leads 52 which are bent from the lead frame 30. The J-leads can then be easily fitted into a mounting socket frequently used on printed circuit boards.

Figure 4:
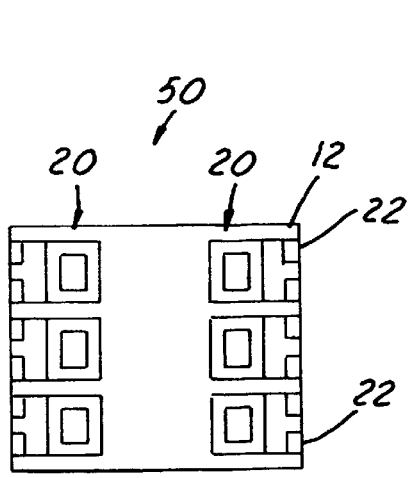
FIG. 4 is an enlarged, plane view of the present invention multi-chip sensing device after the sensing elements are bonded to the substrate.
Figure 4A:
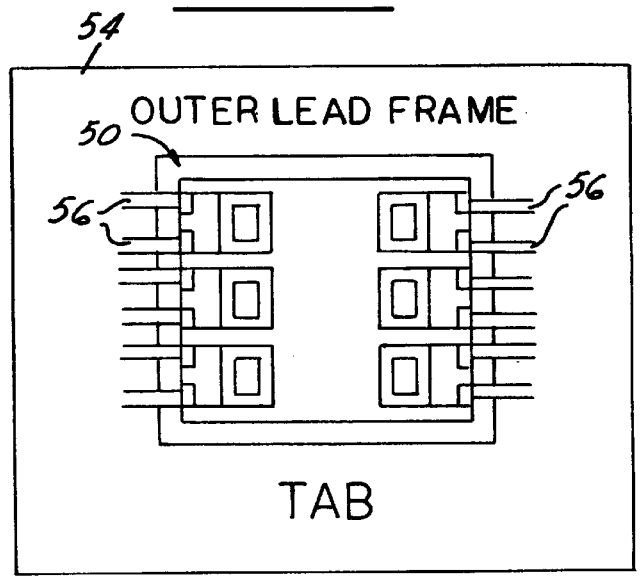
FIG. 4A is an enlarged, plane view of the structure of FIG. 4 after the device is bonded to a flexible circuit board.
Figure 4B:
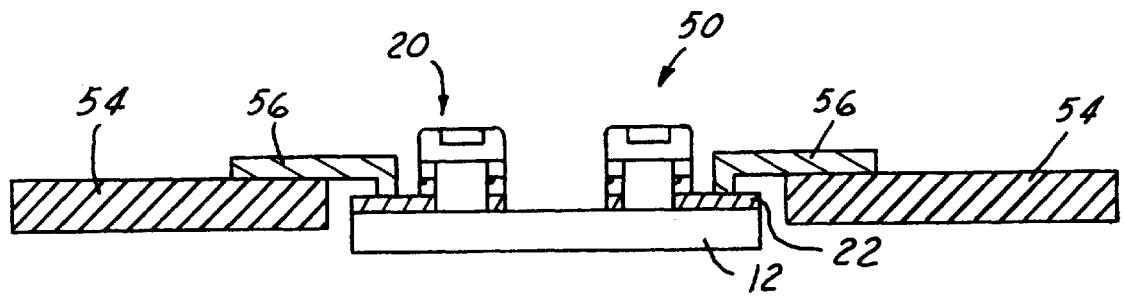
FIG. 4B is an enlarged, cross-sectional view of the structure of FIG. 4 after the device is bonded to a flexible circuit board.

In another alternate embodiment, shown in FIGS. 4, 4A and 4B, a multi-chip sensing device 50 is first formed by bonding a plurality of sensing elements 20 to a substrate 12 through interconnection pads (not shown). The signal output pads 22 are not connected at this point. In the next step of the process, the multi-chip sensing device 50 may be connected in a tape automated bonding (TAB) process to an outer lead frame 54 through a plurality of lead fingers 56. The lead fingers are bonded to the signal output pads 22 by a suitable solder material, such as that containing Pb and Sn.

An enlarged, cross-sectional view of the structure of FIG. 4A is shown in FIG. 4B. It is seen that the lead fingers 56 of the lead frame 54 is connected to the signal output pads 22 formed on the substrate 12. It should be noted that in this configuration, the outer lead frame 54 may be suitably selected as a flexible circuit board fabricated of a flexible plastic material with a conductive foil coating on top. The flexible circuit board is widely used in super-thin electronic devices such as those palm-sized electronic instruments. The method for connection, by using a typical solder material, is similar to that described in the previous embodiments.

Figure 5:
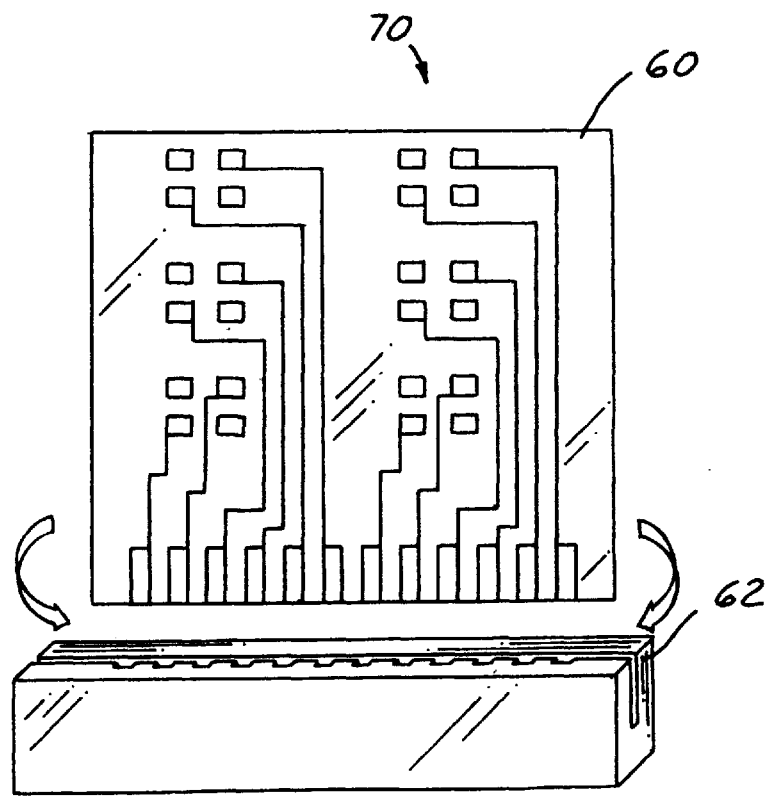
FIG. 5 is a perspective view of the present invention multi-chip sensing device being connected to a socket slot.

The present invention multi-chip sensing device package may further be formed on a substrate 60, such as that shown in FIG. 5. The multi-chip sensing device package 70 can then be inserted into a socket slot 62 by a simple insertion method. The socket slot 62 is normally provided on a printed circuit board for the installation of such device package. This type of mounting device is especially suitable for disposable type sensing elements. For instance, sensing elements which should be replaced after a prolonged usage.

The present invention novel method of forming multi-chip sensing device package and the packages formed have therefore been demonstrated in the above descriptions and in the appended drawings of FIGS. 1~5. It should be noted that, while a piezoelectric quartz crystal sensor is used to illustrate the present invention sensing elements, any other suitable sensing elements may be used in the present invention novel device package.

While the present invention has been described in an illustrative manner, it should be understood that the terminology used is intended to be in a nature of words of description rather than of limitation.

Furthermore, while the present invention has been described in terms of a preferred embodiment, it is to be appreciated that those skilled in the art will readily apply these teachings to other possible variations of the inventions.

The embodiment of the invention in which an exclusive property or privilege is claimed are defined as follows:

1. A multi-chip sensing device comprising:
   an electrically insulative substrate,
   a plurality of bonding sites situated on said substrate, each of said bonding sites comprises at least two interconnection pads adapted for providing electrical communication with a sensing element and at least two signal output pads adapted for outputting signals from said sensing device, said pads being formed of a metal having high electrical conductivity, and
   a plurality of sensing elements bonded to said plurality of bonding sites.

2. A multi-chip sensing device according to claim 1 further comprising a multiplicity of lead fingers emanating from a lead frame bonded to said at least two signal output pads for providing external communication to said multi-chip sensing device.

3. A multi-chip sensing device according to claim 1, wherein said electrically insulative substrate being formed of a ceramic material.

4. A multi-chip sensing device according to claim 1, wherein said electrically insulative substrate being formed of $Al_2O_3$.

5. A multi-chip sensing device according to claim 1, wherein said at least two interconnection pads are formed of Ag/pd.

6. A multi-chip sensing device according to claim 1, wherein said at least two signal output pads are formed of Ag/pd.

7. A multi-chip sensing device according to claim 1, wherein said plurality of sensing elements being adapted for sensing a gas or a liquid.

8. A multi-chip sensing device according to claim 1, wherein said plurality of sensing elements being selected from the group consisting of a piezoelectric quartz crystal sensor, a MOS IC chip sensor and a surface acoustic wave sensor.

9. A multi-chip sensing device according to claim 1, wherein said plurality of sensing elements being bonded to said plurality of bonding sites by a solder containing Sn and Pb.

10. A multi-chip sensing device according to claim 1 further comprising a multiplicity of J-leads bonded to said at least two signal output pads for providing external communication to said multi-chip sensing device.

11. A multi-chip sensing device according to claim 1 further comprising a housing member of insulative material encasing said multi-chip sensing device with top surfaces of said plurality of sensing elements exposed.

12. A multi-chip sensing device package comprising:

a ceramic substrate that is non-electrical-conductive, a plurality of bonding sites on said substrate each adapted for receiving a sensing element, at least two interconnection pads adapted for electrical communication with said sensing element situated on each of said bonding sites, at least two signal output pads adapted for outputting signals from said sensing element situated on each of said bonding sites, a plurality of sensing elements bonded to said plurality of bonding sites, and an insulative housing encasing said multi-chip sensing device while exposing active elements in said plurality of sensing elements.

13. A multi-chip sensing device according to claim 12, wherein said ceramic substrate being formed of $Al_2O_3$.

14. A multi-chip sensing device according to claim 12, wherein said at least two interconnection pads and said at least two signal output pads are formed of Ag/pd.

15. A multi-chip sensing device according to claim 12, wherein said plurality of sensing elements being adapted for sensing gas or liquid.

16. A multi-chip sensing device according to claim 12, wherein said plurality of sensing elements being selected from the group consisting of a piezoelectric quartz crystal sensor, a MOS IC sensor and a surface acoustic wave sensor.

17. A multi-chip sensing device according to claim 12, wherein said plurality of sensing elements being bonded to said plurality of bonding sites by a solder containing Sn and Pb.

18. A multi-chip sensing device package according to claim 12 further comprising a multiplicity of lead fingers emanating from a lead frame bonded to said at least two signal output pads for providing electrical communication with said multi-chip sensing device package.

19. A multi-chip sensing device according to claim 12 further comprising a multiplicity of J-leads bonded to said at least two signal output pads for providing electrical communication with said multi-chip sensing device package.

* * * * *